Dec. 10, 1946. A. CUMMING Plant Pat. 718
CHRYSANTHEMUM
Filed Jan. 2, 1946
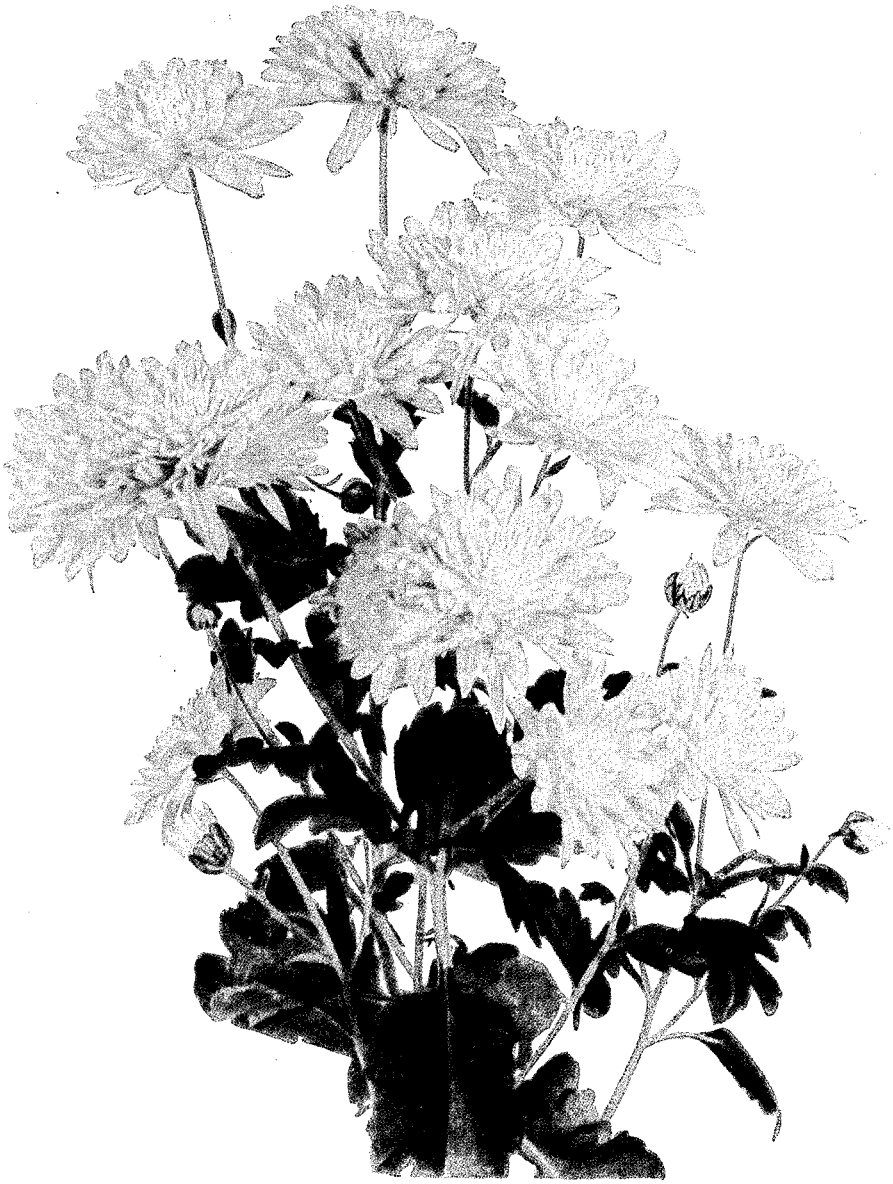
INVENTOR
Alexander Cumming
By Orville M. Kile
plant pat. Agt.

Patented Dec. 10, 1946

Plant Pat. 718

UNITED STATES PATENT OFFICE

718

CHRYSANTHEMUM PLANT

Alexander Cumming, Bristol, Conn., assignor to Bristol Nurseries, Inc., Bristol, Conn., a corporation of Connecticut Application January 2, 1946, Serial No. 638,649

1 Claim. (Cl. 47—60)

My present invention relates to a new and distinct variety of chrysanthemum plant of the decorative pompon type. The color of the flowers of this variety is more brilliant and closer to scarlet than that of any other variety known to me. Other outstanding features of this new variety are the robust growth, together with the prolific production of flowers and their ability to resist frost and remain effective when most other varieties have been spoiled.

My new variety originated in my nurseries at Bristol, Connecticut, as an inbred seedling from one of my seedlings which in turn was derived from a cross of Pompenette by a Korean pompon seedling. I have reproduced the variety by vegetative division and the characteristic features have proved to be permanently fixed.

The accompanying illustration shows a portion of a branch of my new variety containing stems and foliage, together with flowers in various stages of opening. In the original paintings these are shown in approximately their natural size and colors.

In the following detailed description, color plate numbers refer to Ridgway's Color Standards and Nomenclature. Other references to color indicate the ordinary dictionary term.

*The plant*

Growth: Rugged and robust. Densely branching but erect and shapely. Attains a height of about 2 feet. Produces about 15 lateral stems to each branch.

Cold and frost resistance: Very resistant to frost in the open flower; resists moderate freezes which destroy the average chrysanthemum.

Blooming habits: Extremely free-flowering. Production of 75 blossoms to a single branch or spray is not unusual.

Blooming season: From late September to mid-November in this climate.

Stems: Heavy and rigid, branching profusely. Length from 8 to 12 inches from base.

Foliage: Typical chrysanthemum foliage.

*Color.*—Rich, dark green, but not glossy.

*Shape.*—Leaves palmately lobed with 5 main lobes which are bluntly toothed.

*Size.*—Average is approximately 2 inches wide and 3 inches long.

*Texture.*—Substantial.

*Petiole.*—Short, measuring less than ½ inch.

*The flower*

Bud: Small and flat before showing color, becoming urn-shaped. About ½ inch in diameter just before opening.

*Calyx.*—Composed of many heavy scales.

Flower:

*Form.*—Composite flower with very full center. Is of decorative pompon type—rather flat arrangement, not too formal. Has approximately 100 petals or ray flowers which are wide and do not recurve.

*Size.*—Averages about 2 inches in diameter.

*Color.*—Fully opened flower is approximately true Scarlet (Plate I) on the upper side of petals which are then in evidence. Under surface of petals is light tan with an orange tinge. The opening flower has a lighter center which is from Light Orange Yellow to Cadmium Yellow (Plate III).

*Substance.*—Unusually heavy.

*Lasting quality.*—Flowers remain effective when nearly all other kinds have been spoiled by frost. Also keep well as cut flowers.

*Comparison*

The variety most like my new variety is Mandalay, but the two differ chiefly as follows:

1. My new variety is more robust and rugged in growth.
2. My new variety is more resistant to frost and cold.
3. The flowering season of my variety is much longer.
4. My new variety is much more free-flowering and a more prolific producer of good flowers.
5. The color of the flowers of my new variety is more brilliant and closer to scarlet.

Having thus disclosed my invention, I claim:

The new and distinct variety of chrysanthemum plant substantially as shown and described, characterized particularly by its robust and rugged growth; its extremely free-branching and free-flowering habits; its long flowering season; its resistance to frost and cold which enables the flowers to remain effective for an unusually long period; and the approximately true scarlet color of its medium-sized flowers.

ALEXANDER CUMMING.